(12) United States Patent
Laprade

(10) Patent No.: US 7,081,618 B2
(45) Date of Patent: Jul. 25, 2006

(54) USE OF CONDUCTIVE GLASS TUBES TO CREATE ELECTRIC FIELDS IN ION MOBILITY SPECTROMETERS

(75) Inventor: Bruce Laprade, Holland, MA (US)

(73) Assignee: Burle Technologies, Inc., Wilmington, DE (US)

( * ) Notice: Subject to any disclaimer, the term of this patent is extended or adjusted under 35 U.S.C. 154(b) by 94 days.

(21) Appl. No.: 10/807,718

(22) Filed: Mar. 24, 2004

(65) Prior Publication Data

US 2005/0211894 A1 Sep. 29, 2005

(51) Int. Cl.
*H01J 49/26* (2006.01)
*B01D 59/44* (2006.01)

(52) U.S. Cl. .................. 250/286; 250/281; 250/287; 250/288

(58) Field of Classification Search .............. 250/286, 250/287, 281, 288
See application file for complete search history.

(56) References Cited

U.S. PATENT DOCUMENTS

| | | | |
|---|---|---|---|
| 4,390,784 A | 6/1983 | Browning et al. | |
| 4,712,008 A | 12/1987 | Vora et al. | |
| 4,777,363 A | * 10/1988 | Eiceman et al. | 250/286 |
| 5,021,654 A | * 6/1991 | Campbell et al. | 250/287 |
| 6,008,491 A | 12/1999 | Smentkowski et al. | |
| 6,369,383 B1 | 4/2002 | Cornish et al. | |
| 6,607,414 B1 | 8/2003 | Cornish et al. | |
| 2003/0230726 A1 | 12/2003 | Van Der Verr et al. | |

OTHER PUBLICATIONS

"Resistive Glass Products", Product Data Sheets EP111 (Dec. 2003), © Burle Technologies, Inc., Lancaster, PA.
Gary Alan Eiceman et al., "Ion Mobility Spectrometry", pp. 88–118, CRC Press, Inc., 1994.
Bruce N. Laprade, "The Development of Novel Resistive Glass Technology to Simplify Reflectron Lens, Ion Guide, Drift Tubes and Ion Source Designs in Mass Spectrometers"; Abstract and slides from presentation held at The 2004 Pittsburgh Conference, Mar. 7, 2004.

* cited by examiner

*Primary Examiner*—Nikita Wells
(74) *Attorney, Agent, or Firm*—Dann, Dorfman, Herrell and Skillman, P.C.

(57) ABSTRACT

An ion mobility spectrometer is described in which the reaction-ionization chamber and/or the ion drift chamber are constructed with one or more single-piece glass tubes. The inner surface of the tube is rendered electrically conductive by thermal and/or chemical treatment thereof. The glass tube(s) are used in place of the stack assemblies of metal and ceramic annular components that typically used in such devices. The use of the glass tube(s) provides a significant reduction in the number of parts used in such spectrometers, simplification in their manufacture, and improvements in their performance and reliability.

24 Claims, 6 Drawing Sheets

USE OF CONDUCTIVE GLASS TUBES TO CREATE ELECTRIC FIELDS IN ION MOBILITY SPECTROMETERS

FIELD OF INVENTION

This invention relates to spectrometers used for chemical identification and assaying of sampled analytes. More specifically, the present invention relates to ion mobility spectrometers with regard to their design and methods of construction. In particular, the invention relates to the use of conductive glass tube sections as components of ion drift tubes and reaction-ionization chambers in ion mobility spectrometers.

BACKGROUND OF THE INVENTION

The ion mobility spectrometer is an instrument used for identification and analysis of chemical species, especially trace amounts of substances dispersed in a vapor phase such as the atmosphere or ambient of a reactor or analysis chamber. The ion mobility spectrometer emerged from developments in the late 1960's and early 1970's, and is now a well-established technology for defense and civilian applications. The technology continues to evolve as its use widens from specialized military equipment and laboratory instrumentation to serve more varied applications including those related to environmental monitoring, law enforcement, process control, and industrial hygiene and safety. In particular, ion mobility spectrometers are being used more frequently in trace analysis of explosives, narcotics, and biochemical warfare agents. Ion mobility spectrometers have gained broad acceptance in niche markets due to their relatively low cost, simple operation, and reliability. Moreover, ion mobility spectrometers are well-suited for miniaturization, portable deployment, and high-volume mass production. Even wider utilization of ion mobility spectrometers is expected with further reductions in their size, cost, and complexity. The present invention addresses these aspects of design and construction, leading to broad based improvements in ion mobility spectrometer technology.

SUMMARY OF THE INVENTION

The present invention provides a novel way to construct an ion mobility spectrometer, wherein the ion drift tube and reaction-ionization chamber are formed of single-piece, conductive glass tubes. The conductive glass tubes are made by forming a conductive surface layer in otherwise high resistivity glass using various thermal and chemical treatments including annealing at elevated temperatures in a hydrogen ambient. Glass tubes made in such a manner can be used for creating electric fields to accelerate and separate ions in ion mobility spectrometers. The conductive glass tubes are metallized and tabbed at each end so that a high voltage can be imposed across the length of the tube, creating a substantially uniform axial electric field within the tube. As such, conductive glass tubes serve as replacements for the stacked metal and ceramic ring structures that are employed in the known ion mobility spectrometers. The use of the conductive glass tube provides the advantages of simpler manufacture, more uniform electric fields, enhanced ruggedness, less maintenance, and lower costs, relative to the known devices.

BRIEF DESCRIPTION OF THE DRAWINGS

The foregoing summary as well as the following detailed description will be better understood with reference to the drawings in which.

DETAILED DESCRIPTION

In the present invention, a single-piece glass tube in which the surface conductivity has been modified replaces one or several subassemblies of a conventional ion mobility spectrometer. Specifically, the ion drift tube and the reaction-ionization chamber of an ion mobility spectrometer are both typically constructed as an assembled stack of alternating insulating (e.g., ceramic) and conducting (e.g., metal) annular rings aligned along a common axis. According to the present invention, such a ring assembly is replaced by a glass tube in which the inner surface is rendered electrically conductive by a chemical and/or thermal treatment. The treatment chemically modifies the glass and converts a shallow surface layer on the glass from a highly electrically insulating material to a semiconducting material.

Figure 1:
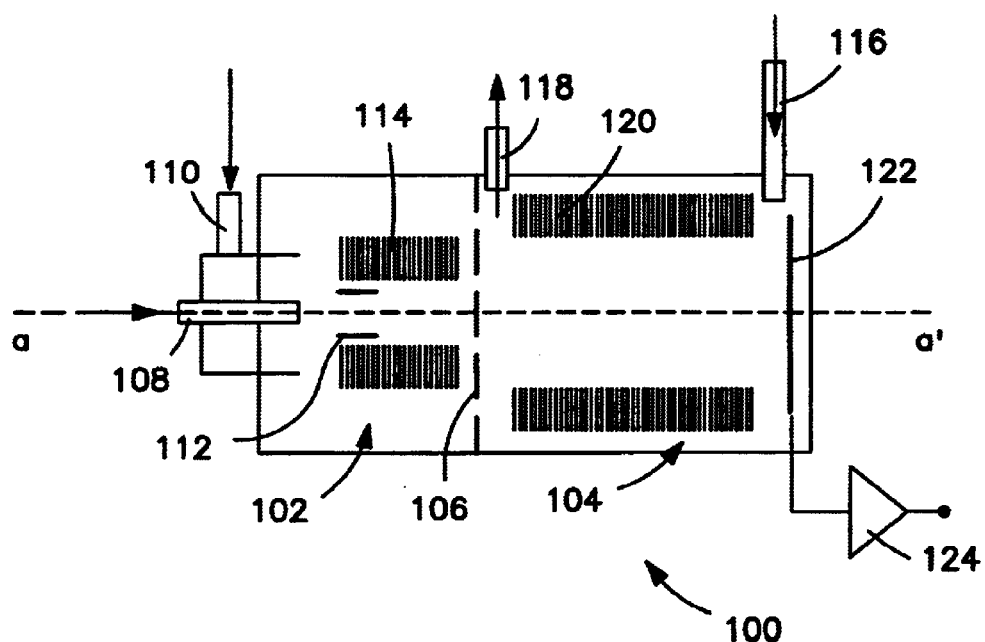
FIG. 1 is a schematic diagram of a known ion mobility spectrometer.

FIG. 1 shows a schematic of a known ion mobility spectrometer 100 having the essential structural features of such instruments. The major components of the instrument include a reaction-ionization chamber 102 and an ion drift tube section 104 that are separated from each other by a shutter grid electrode 106. The reaction-ionization chamber 102 and ion drift tube 104 are typically cylindrical-shaped, abutted end-to-end, and connected through an orifice. The reaction-ionization tube 102 and ion drift tube 104 are aligned along a common axis a–a'. It is noted, however, that the diameters and lengths of the reaction-ionization tube and ion drift tube may be substantially different. The passage of ions between the ionization-reaction chamber and ion-drift tube is gated by the shutter grid electrode 106.

In operation, a volatile sample is injected into the reaction-ionization chamber 102 through a sample inlet port 108, where it is mixed with a carrier gas introduced through a gas inlet port 110. A beta-particle source 112, such as a radioactive nickel, is disposed within the reaction-ionization chamber and emits beta particle radiation that ionizes gas-phase molecules in the reaction-ionization chamber 102. The reaction-ionization chamber 102 is formed of a cylindrical stack 114 of metal rings, often termed "guard rings". The metal rings are separated from each other by insulating ceramic spacers to form an electrode structure. The metal guard rings are series-connected by high-impedance resistors (not shown). The interior space defined by the stack of guard rings and spacers constitutes the reaction-ionization chamber. When a voltage is imposed across the ends of the stack, an electric field is generated inside the cylindrical stack. The electric field accelerates the ions generated in the interior of the stack toward the shutter electrode 106. A voltage applied to the shutter electrode permits or impedes the passage of ions to the ion drift tube 104 depending on the charge of the ion and the polarity and magnitude of the voltage applied to the grid. Ions admitted into the ion drift tube substantially follow a trajectory parallel to axis a–a'.

A stack 120 of metal guard rings and ceramic spacers, similar in construction to the stack 114, is disposed along the axis a–a' to form the drift tube 104. A voltage applied to the ends of the stack 120 creates an electric field along axis a–a'. The ions are thereby accelerated toward an ion detector 122 located at the end of the ion drift tube 104. The ion drift tube is continually purged with a drift gas injected through port 116. Port 118 serves as an exhaust for the sample, carrier, and drift tube gases. The electric field applies a force to the ions, which is tempered by random scattering of the ions with the molecules of the drift gas injected in port 116. For a particular electric field and ambient carrier gas species, partial pressure, and temperature, ions attain a characteristic drift velocity which is related to the nature of the ion, including its charge and effective scattering cross-section. Therefore, the drift time for an ion to traverse the ion-drift tube, from the shutter 106 to ion detector 122 is characteristic of a particular ion and serves to identify the ion. The ion detector 122 is often a Faraday cup type device, wherein a charge or current is induced upon impact of an ion with a plate surface of the detector. The induced charge or current is detected by an external circuit 124 such as an electrometer. The sample can be quantitated based on the assumption that the detector current is proportional to the number of ions striking the detector in a time interval that corresponds to the arrival time, with sufficient allowance for inevitable broadening of the arrival time, for a particular species of the sample.

Figure 2:
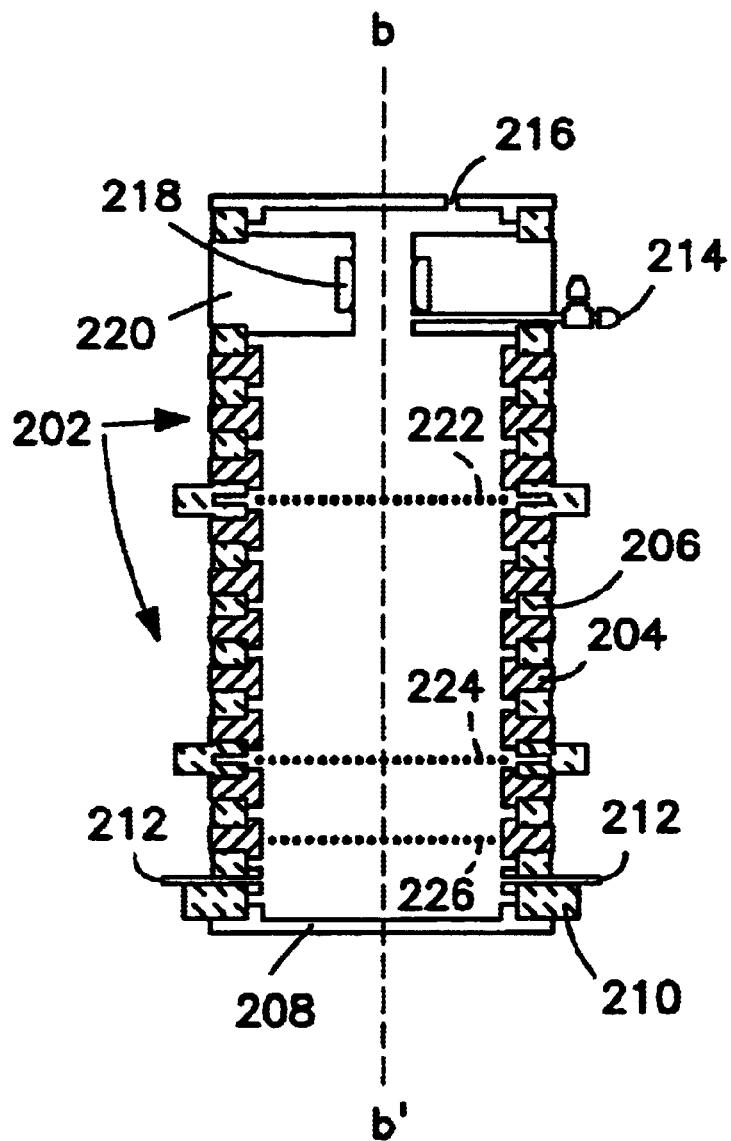
FIG. 2 is a side elevation view, in partial section, of a physical embodiment of a drift tube used in an ion mobility spectrometer.

FIG. 2 shows a known construction for an ion drift tube of an ion mobility spectrometer and its disposition to adjacent components of the spectrometer. The ion drift tube 202 has a stack of metal guard rings 204 and ceramic spacers 206 disposed between respective pairs of the guard rings 204. The guard rings can be made from various metals including, for example, stainless steel. In the arrangement shown in FIG. 2, the drift tube 202 has ten metal guard rings. One end of the ion drift tube is capped with a collector plate 208 to detect ions. The collector plate 208 may be connected to an electrometer (not shown). The collector plate 208 is electrically isolated from the guard ring electrodes by a nonconducting spacer 210. The nonconducting spacer 210 is preferably formed of polytetrafluoroethylene (PTFE) material (e.g., TEFLON®). The assembly includes ports for the drift gas inlet 212, the sample gas inlet 214, and gas exhaust 216. A nickel (isotope 63) beta particle source 218 is embedded in a ceramic insulator 220 located at the front end of the drift tube 202. One or more gating electrodes 222, 224, and 226 that provide control of ion currents through the drift tube are disposed at various positions along the axis of the drift tube 202.

Figure 3:
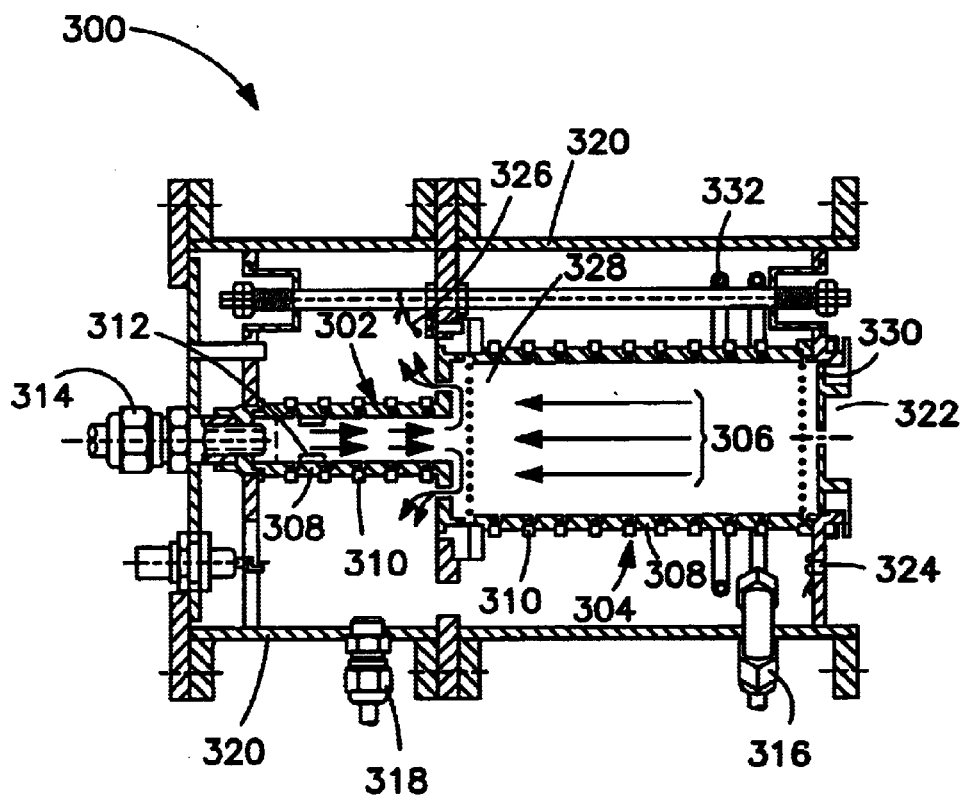
FIG. 3 is a side elevation view, in partial section, of a physical embodiment of the ion mobility spectrometer shown in FIG. 1.

FIG. 3 shows a physical arrangement of a known ion mobility spectrometer 300 with a reaction-ionization sector 302 that is abutting, but separate from the ion drift tube sector 304. A drift region electric field 306 is created by biasing the stack of metal guard rings 308 separated by machinable glass ceramic insulating rings 310. A coaxial stack of electrodes of smaller diameter and overall length defines the reaction-ionization chamber 302. Ports for the sample/carrier gas inlet 314, drift gas inlet 316, and exhaust 318 are tapped into the instrument casing 320. A nickel foil beta radiation source 312 is embedded in the sidewall of the reaction-ionization tube 302 proximal to the sample/carrier gas inlet 314. A Faraday plate 322 is disposed at the back end of the ion drift tube sector 304 and serves as the ion detector. Thermocouples 324 and 326 are arrayed at locations inside the spectrometer 300 for monitoring the temperature of the ion drift region and reaction-ionization region, respectively. A shutter grid 328 disposed adjacent the inlet end of the ion drift tube 304 and an aperture grid 330 disposed at the back end of the ion drift tube 304, provide control of the ion current in the ion drift region. Heating or cooling elements 332 can be wrapped around the ion drift tube region to control the temperature of the ion drift tube ambient.

Figure 4:
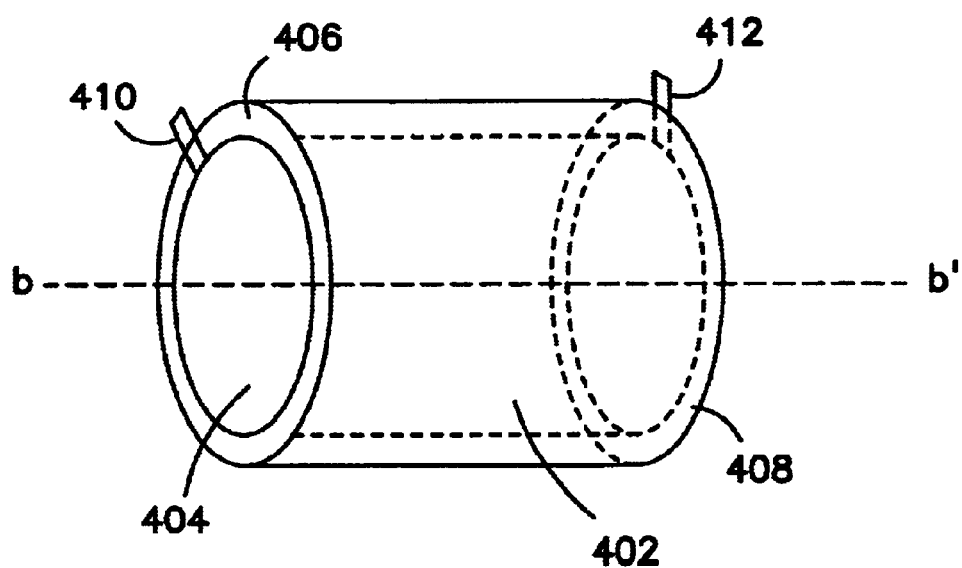
FIG. 4 is a schematic diagram of a conductive glass tube used in an ion mobility spectrometer according to the present invention.

A novel feature of the ion mobility spectrometer according to the present invention is the replacement of the stacks of metal rings and ceramic spacers used in the known devices with single-piece conductive glass tubes. FIG. 4 shows a glass tube 402 of the type use in an ion mobility spectrometer according to the present invention. The glass tube 402 has an inside surface 404 that is rendered semiconducting by a thermal-chemical treatment described hereinbelow. A thin film of metal is deposited on each end of the tube, forming annular electrodes 406 and 408. Conductive tabs 410 and 412 are attached to electrodes 406 and 408, respectively, so that the electrodes can be connected to a high-voltage source. A voltage impressed across the ends of the tube creates an electric field which is aligned along the axis b–b' of the tube. The direction of the axial electric field can be easily reversed by changing the polarity of the applied voltage. As such, this electric field constitutes the drift field used to separate ions of a sample mixture on the basis of their ion mobilities in the ion drift tube section of an ion mobility spectrometer.

When a voltage is imposed across the ends of the glass tube 402, the relatively high resistivity of the surface layer sustains an electric field both interior and exterior to the conductive surface layer of the tube. The exterior electric field is similar to the fringing field formed around the periphery of capacitor plates. Due to the cylindrical symmetry of the conductive surface layer, the resultant electric field in the interior space of the conductive glass tube is substantially uniform in strength and aligned parallel to the axis of the tube.

The conductive glass tube 402 can also be used to form the reaction-ionization chamber of an ion mobility spectrometer. In that case, an axial electric field forces the ionized particles towards the shutter electrode, where they can be gated into the ion drift tube. Glass materials, such as lead oxides, lead silicates, or metal silicates, are inherently electrically insulating as they are essentially devoid of the free charge carriers needed to constitute an electric current induced in response to an imposed electric field. However, surface layers of glass can be rendered electrically conductive by certain chemical treatments and/or thermal processes. For instance, a reduction process, whereby the glass workpiece is annealed in a reducing hydrogen atmosphere, can chemically modify the surface of the glass. This chemical transformation creates a shallow surface region with some combination of non-stoichiometry, defects, and electrically active dopant impurities that produce an increased density of free charge carriers and a consequent enhanced electrical conductivity. However, the invention is not specific to, nor dependent on, a particular mechanism that converts a surface region of a highly insulating glass to a semiconducting surface layer of increased conductivity.

The tubes are preferably formed of any of a number of known glasses including, but not limited to, lead glasses such as MCP-10, L2LN, MCP-9, MCP-12, RGS 65-12. RGS 66-41, and RGS 74-12, all of which are made and sold by Burle Industries Inc., or from lead silicate glasses such as GE 821, made and sold by General Electric Co., or Corning 8161 and Corning 8165, made and sold by Corning Glass Co. In addition, any metal silicate glass, or more generally, any metal oxide glass, which can be made conductive through a chemical and/or thermal process is a viable material for the applications described herein.

Common to all approaches within the scope of the invention is the application of a process to create a conducting layer on the inner surface of a glass tube. As a specific example, a lead silicate tube is subjected to a reduction process in order to make the glass semiconductive. TRAP (*Acta Electronica* [1971] 14, 141–77) describes a typical hydrogen reduction process used to make alkali-doped silica glass electrically conductive. The details of this process are well known to manufacturers of microchannel plates, channel electron multipliers, and x-ray tubes. Briefly, the hydrogen reduction process entails loading the glass workpiece into a closed furnace which is purged with pure hydrogen or a controlled mixture of hydrogen and oxygen. The temperature is slowly increased from room temperature at a rate of 1 to 3° C. per minute. As the temperature reaches approximately 250° C., the lead oxide in the glass is chemically reduced to a semiconductive state. This conversion of lead oxide to a reduced state occurs initially in a region within a depth of a few hundred angstroms from the exposed surface of the glass. Continued heating and exposure to hydrogen results in a deeper chemical-reduced, conductivity-enhanced layer and lower sheet resistances. The sheet resistivity of the glass can be controlled in a precise and reproducible manner by control of the time-temperature schedule of the furnace, exposure time, and ambient gas composition, pressure, and flow rate. The technique is thus very similar to dopant impurity diffusion processes used in silicon microelectronics technology to form surface layers of a specified conductivity such as comprise the emitters of diodes and transistors.

All glass surfaces exposed to the reducing ambient are converted to a more conductive state. Conductive surface regions can be selectively stripped by chemical etching or mechanical abrasion, such that a pattern of conductive and highly resistive regions can be formed in the surface of the glass.

The following particular set of process parameters are representative of the methods used herein. A three-hour ramp up of the reducing furnace from room temperature to 200° C., a 1-hour ramp up to 300° C., 12.5-hour ramp up to 445° C., a soak (temperature held constant) at 445° C. for three hours, followed by cool-down to room temperature. The furnace ambient pressure is at 34 psi (pounds per square inch) with continuous purging with hydrogen at a flow rate of 40 liters per minute. For a specific glass, a high-temperature limit is imposed by the sag point of the glass. A minimum temperature is selected at which some perceptible change, such as a change in surface appearance or sheet resistivity is evident.

The electrical resistance of glass tubes may be varied by as much as six orders of magnitude, from $10^5$ to $10^{11}$ Ohms, by changing the processing parameters such as temperature, exposure time, gas pressure, and flow rate. Electrical connection to the tube is preferably accomplished by depositing a thin film of a nickel-chromium alloy, a nickel-iron alloy, copper, a copper alloy, gold, or any other suitable metal on the edges of the tube. Conductive tabs can be attached to the thin film electrodes by soldering or wire bonding.

Figure 5:
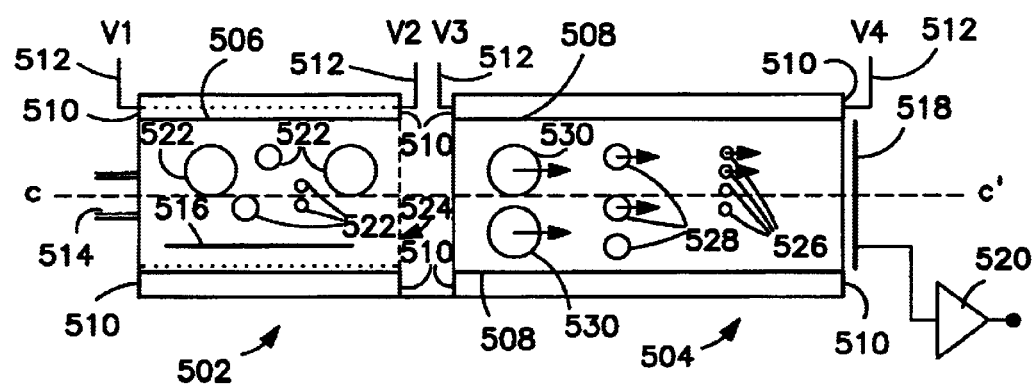
FIG. 5 is a schematic view of an arrangement of a conductive glass tube reaction-ionization chamber and a conductive glass tube ion drift tube as used in an ion mobility spectrometer according to the present invention.

Single-piece conductive glass tubes can be incorporated into ion mobility spectrometers in various ways. FIG. 5 shows a preferred arrangement of an ion mobility spectrometer wherein a first conductive glass tube 502 is used to form the reaction-ionization chamber, and a second conductive glass tube 504, but generally of diameter and length different from conductive glass tube 502, is used as the ion drift tube. The reaction-ionization tube and ion drift tube are substantially aligned along a common axis c–c'. The inside surface 506 of first conductive tube 502 has been rendered conductive by a thermal/chemical treatment. Likewise, the inside surface 508 of the second conductive tube 504 has also been rendered conductive by the thermal/chemical processes, although separate and distinct treatments for each tube can be performed in order to optimize their respective function in the ion mobility spectrometer. As described above, the ends 510 of the tubes are metallized by depositing a layer of a conductor, such as a nickel-chromium steel or gold. Connecting tabs 512 permit the application of voltages V1, V2, V3, and V4 at the ends of the conductive glass tubes. Sample material for analysis is introduced into the reaction-ionization chamber through an inlet port 514. An ionization source 516, usually in the form of a foil made of beta-emitting, radioactive material is positioned in the reaction-ionization chamber. A detector plate 518 detects the arrival of ions at the end of the ion drift tube. The impact of an ion on the detector plate generates a current pulse that is detected by external circuitry 520 when the electrical current flows from the detector plate 508 to the external circuit 520. The sample is composed of molecules of various sizes 522, and thus the ionized sample confined in the reaction-ionization chamber will generally be composed of ions of distinct mobilities. A shutter grid 524 gates the passage of ions between the reaction-ionization tube and the ion drift tube as described above with reference to the known devices.

If positively-charged ions are to be analyzed, then V1 is grounded, a negative voltage is applied to V2, and at a predetermined time, a high negative voltage pulse is applied to the shutter grid 524 enabling all positively-charged ions to enter the ion drift tube 504. A negative voltage is applied to V3, and a negative voltage of greater magnitude is applied to V4 in order to accelerate the positive ions toward the detector 518. The voltage difference between V3 and V4 creates the ion drift electric field.

If negatively-charged ions are to be analyzed, then V1 is grounded, a positive voltage is applied to V2, and at a predetermined time, a high positive voltage pulse is applied to the shutter grid enabling all negatively-charged ions to enter the ion drift tube 504. A positive voltage is applied to V3, and a positive voltage of greater magnitude is applied to V4 in order to accelerate the negative ions toward the detector 518.

In both modes of operation, the respective ions separate based on their size because smaller ions 526 have the higher mobility than larger ions and will arrive at the detector first, followed by ions of an intermediate size 528, and lastly followed by the largest ions 530 of the sample. Further, the detector signal amplitude is proportional to the number of ions.

Figure 6:
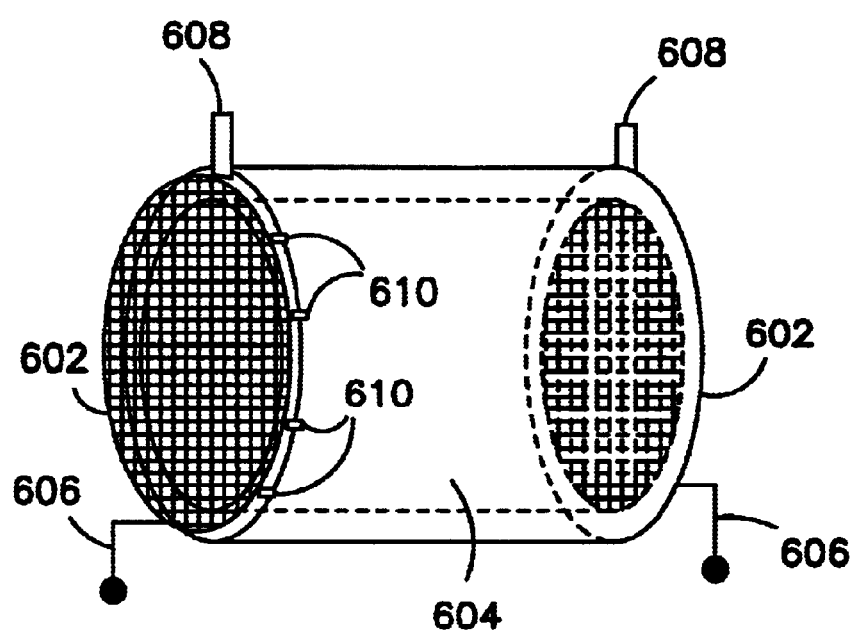
FIG. 6 is a schematic view of a conductive glass tube member with ion shutter grids, in the form of metal meshes, attached to both ends thereof.

The shutter grid or shutter grids that are typically incorporated into the structure of an ion mobility spectrometer can be directly attached to one or both ends of the conductive glass tube that functions as the ion mobility drift tube, as well as one or both ends of the conductive glass tube that serves as the reaction-ionization chamber. The grid is preferably made in the form of a mesh structure, such as a metal wire screen, or a metal sheet perforated with a series of holes. As an example of such, FIG. 6 shows the positioning of a metal grid 602 on the ends of a conductive glass tube 604, in such a manner that when the ion mobility spectrometer is assembled, the metal mesh can be connected to a modulated electrical voltage source (not shown) with electrical leads 606. The electrical leads 606 for the shutter grid are typically separate from the leads 608 used to impose the voltage bias that creates the axial field of the interior region so defined by the tube 604, or optionally in some cases, the shutter grid leads and tube axial field bias leads can be common. The shutter grid can be isolated from the glass tube using insulating standoffs 610. The shutter grid is attached to the glass tubular member using any number of techniques for making a glass-to-metal bond or seal, as are well known in the art of high-vacuum technology and glass blowing. For instance, the glass can be heated to soften it at points where a protrusion, insulating standoff, tab, or part of the metal shutter grid can be impressed into the softened glass and fused to make a permanent bond. Alternatively, the shutter grid can be attached by soldering a section of the grid to metal pads deposited on the glass member, formed in a way similar to the tabs used to apply a voltage bias to the conductive glass tube.

It will be recognized by those skilled in the art that changes or modifications may be made to the above-described embodiments without departing from the broad inventive concepts of the invention. It is understood, therefore, that the invention is not limited to the particular embodiment which is described, but is intended to cover all modifications and changes within the scope and spirit of the invention as described above and set forth in the appended claims.

What is claimed:

1. An ion mobility mass spectrometer comprising:
    a glass tube, with an interior conductive surface, and having an interior space defining an ion drift region;
    means for injecting a sample material into the ion drift region;
    means for ionizing the sample material inside the ion drift region;
    an ion detector disposed at one end of said glass tube; and
    means for generating an electric field within the ion drift region,
    whereby an ion of the sample material is accelerated through the ion drift region toward said ion detector.

2. An ion mobility spectrometer as set forth in claim 1 wherein the means for generating the electric field comprises
    a first electrode formed on a first end of the glass tube;
    a second electrode formed on a second end of the glass tube; and
    a voltage source operatively connected to said first and second electrodes.

3. An ion mobility spectrometer as set forth in claim 2 wherein the first and second electrodes each comprise a thin metal film.

4. An ion mobility spectrometer as set forth in claim 3 wherein the thin metal film is formed of a metal selected from the group consisting of nickel-iron alloys, nickel-chromium alloys, copper, copper alloys, and gold.

5. An ion mobility spectrometer as set forth in claim 1 wherein the glass tube is formed of a lead glass or a metal oxide glass.

6. An ion mobility spectrometer as set forth in claim 5 wherein the metal oxide glass is a metal silicate glass.

7. An ion mobility spectrometer as set forth in claim 1 wherein said glass tube has a second interior space that defines a reaction-ionization chamber wherein the sample material is injected and the means for ionizing the sample material is located.

8. An ion mobility spectrometer as set forth in claim 7 comprising a shutter grid electrode disposed in said glass tube between the reaction-ionization chamber and the ion drift region.

9. An ion mobility spectrometer as set forth in claim 8 comprising means for energizing said shutter grid electrode.

10. An ion mobility spectrometer as set forth in claim 7 comprising a metal mesh disposed at an end of the second interior space of the glass member that defines the reaction-ionization chamber, said metal mesh being adapted for connection to a modulated electrical voltage source, whereby said mesh acts as an ion shutter grid when energized by said voltage source.

11. An ion mobility spectrometer as set forth in claim 1 comprising:
    a second glass tube having an interior conductive surface, said second glass tube being substantially cylindrical in shape, and having an interior space defining a reaction-ionization chamber having an inlet end and an outlet end;
    means for injecting a sample material into the inlet end of the reaction-ionization chamber; and
    means disposed in the reaction-ionization chamber for ionizing the sample material.

12. An ion mobility spectrometer as set forth in claim 1 comprising a metal mesh attached to an end of the glass member and adapted for connection to a modulated electrical voltage source, whereby said mesh acts as an ion shutter grid when energized by said voltage source.

13. An ion mobility mass spectrometer comprising:
    a first glass tube having an interior conductive surface, said first glass tube being substantially cylindrical in shape, and having an interior space defining a reaction-ionization chamber having an inlet end and an outlet end;
    means for injecting a sample material into the inlet end of the reaction-ionization chamber;
    means disposed in the reaction-ionization chamber for ionizing the sample material;
    a second glass tube having an interior conductive surface, said second glass tube being substantially cylindrical in shape, having an interior space defining an ion drift region having an inlet end and an outlet end, the inlet end of the second glass tube facing the outlet end of the first glass tube;
    means for controlling flow of ions from the reaction-ionization chamber into the ion drift region;
    an ion detector disposed adjacent to the outlet end of the ion drift region; and
    means for generating electric fields within the reaction-ionization chamber and the ion drift region, whereby an ion of the sample material is accelerated through the reaction-ionization chamber and through the ion drift region toward said ion detector.

14. An ion mobility spectrometer as set forth in claim 13 wherein the means for generating the electric fields comprises
    a first electrode formed on a first end of the first glass tube;
    a second electrode formed on a second end of the first glass tube;
    a voltage source operatively connected to said first and second electrodes;

a third electrode formed on a first end of the second glass tube;

a fourth electrode formed on a second end of the second glass tube; and a second voltage source operatively connected to said third and fourth electrodes.

15. An ion mobility spectrometer as set forth in claim 14 wherein the first, second, third, and fourth electrodes each comprises a thin metal film.

16. An ion mobility spectrometer as set forth in claim 15 wherein the thin metal film is formed of a metal selected from the group consisting of nickel-iron alloys, nickel-chromium alloys, copper, copper alloys, and gold.

17. An ion mobility spectrometer as set forth in claim 13 wherein the first and second glass tubes are formed of a lead glass or a metal oxide glass.

18. An ion mobility spectrometer as set forth in claim 17 wherein the metal oxide glass is a metal silicate glass.

19. An ion mobility spectrometer as set forth in claim 13 wherein the means for controlling the flow of ions comprises a shutter grid electrode disposed between the outlet end of the reaction-ionization chamber and the inlet end of the ion drift region.

20. An ion mobility spectrometer as set forth in claim 19 comprising means for energizing said shutter grid electrode.

21. An ion mobility spectrometer as set forth in claim 1 wherein the interior conductive surface of the glass tube comprises aa pattern of conductive and resistive regions formed in the surface of the glass.

22. An ion mobility spectrometer as set forth in claim 10 wherein the interior conductive surface of the second glass tube comprises a pattern of conductive and resistive regions formed in the surface of the glass.

23. An ion mobility spectrometer as set forth in claim 11 wherein the interior conductive surface of the first glass tube comprises a pattern of conductive and resisti e regions formed in the surface of the glass.

24. An ion mobility spectrometer as set forth in claim 11 wherein the interior conductive surface of the second glass tube comprises a pattern of conductive and resistive regions formed in the surface of the glass.

* * * * *